US00PP19136P2

(12) United States Plant Patent
Van Blokland

(10) Patent No.: US PP19,136 P2
(45) Date of Patent: Aug. 19, 2008

(54) ***ACONITUM* PLANT NAMED 'BLUE LAGOON'**

(50) Latin Name: ***Aconitum* hybrid**
Varietal Denomination: Blue Lagoon

(75) Inventor: Robbert G. C. Van Blokland, De Hoef (NL)

(73) Assignee: Inspiration Plant, De Hoef (NL)

( * ) Notice: Subject to any disclaimer, the term of this patent is extended or adjusted under 35 U.S.C. 154(b) by 0 days.

(21) Appl. No.: 11/653,547

(22) Filed: Jan. 16, 2007

(51) Int. Cl.
*A01H 5/00* (2006.01)

(52) U.S. Cl. ..... Plt./397; Plt./263

(58) Field of Classification Search ..... Plt./397, Plt./263

See application file for complete search history.

*Primary Examiner*—Annette H Para
*Assistant Examiner*—S. B. McCormick-Ewoldt
(74) *Attorney, Agent, or Firm*—Jondle & Associates, P.C.

(57) ABSTRACT

A new *Aconitum* plant particularly distinguished by several medium sized violet-blue flowers situated above the foliage, uniform green foliage with large palmate leaves, a tall, narrow, upright habit and hardiness to at least USDA zone 4, is disclosed.

2 Drawing Sheets

Genus and species: *Aconitum* hybrid.
Variety denomination: 'Blue Lagoon'.

BACKGROUND OF THE NEW PLANT

The present invention comprises a new and distinct cultivar of *Aconitum,* botanically known as *Aconitum* interspecific hybrid, and hereinafter referred to by the cultivar name 'Blue Lagoon'. The new cultivar originated as a seedling from a cross between the female parent *Aconitum cammarum* 'Bicolor' (unpatented), while the male parent was the *Aconitum henryi* 'Spark's Variety' (unpatented).

The new cultivar was created as a seedling and originated in the breeder's nursery in De Hoef, The Netherlands and has been asexually reproduced repeatedly by tissue culture and softwood cuttings in De Hoef, The Netherlands. The present invention has been found to retain its distinctive characteristics through successive asexual propagations.

Plant Breeder's Rights for this cultivar were applied for with the European Union on Oct. 6, 2006.

SUMMARY OF THE INVENTION

The following are the most outstanding and distinguishing characteristics of this new cultivar when grown under normal horticultural practices in the Netherlands.

1. Violet-blue flowers;
2. Several medium sized flowers, situated above the foliage;
3. Uniform, green foliage with large, palmate leaves;
4. A compact, narrow and upright habit; and
5. Hardy to at least USDA zone 4.

DESCRIPTION OF THE PHOTOGRAPHS

This *Aconitum* is illustrated by the accompanying photographs which show overall plant habit, flowers, and foliage of the plant; the colors shown are as true as can be reasonably obtained by conventional photographic procedures. The photographs are from a whole plant about 1 year old and grown in a 17 cm pot outdoors in the Netherlands.

DESCRIPTION OF THE NEW CULTIVAR

Figure 1:
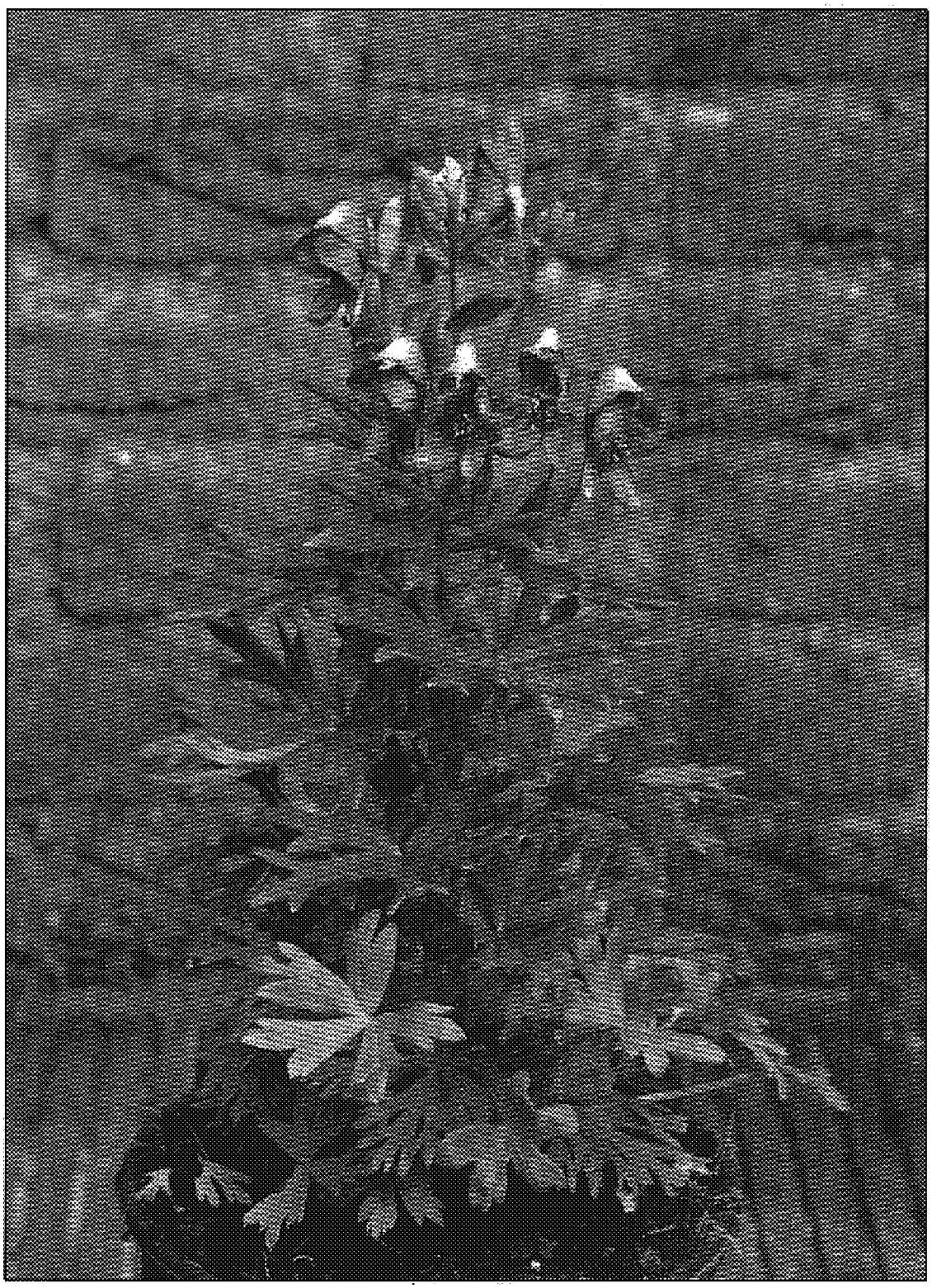
FIG. 1 shows the overall plant habit, including the flowers and foliage.
Figure 2:
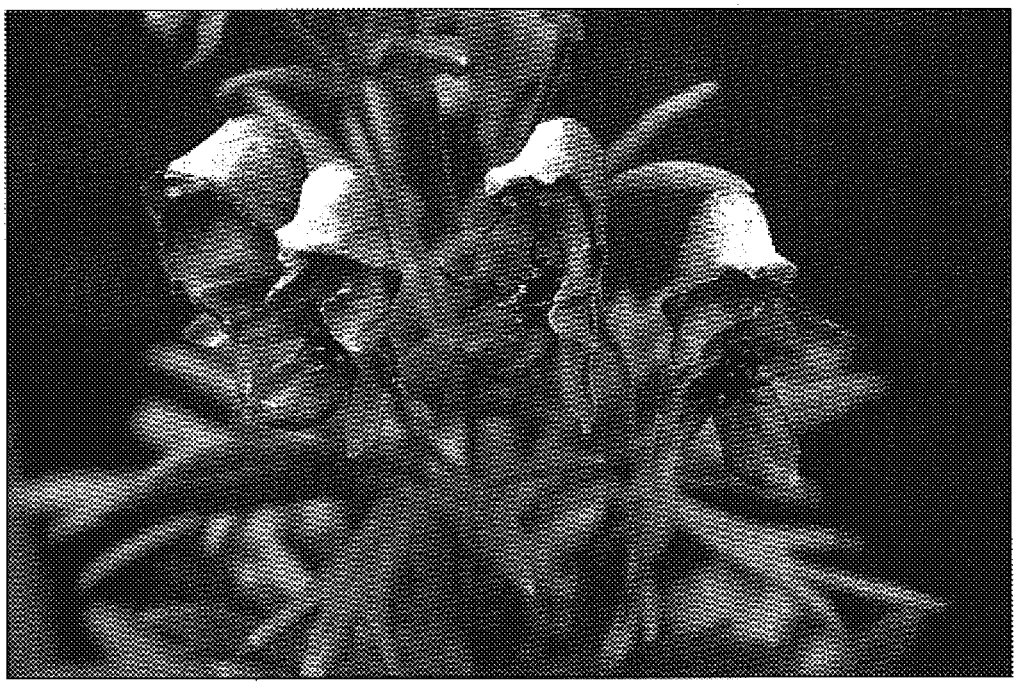
FIG. 2 shows a close-up of the mature flowers.
Figure 3:
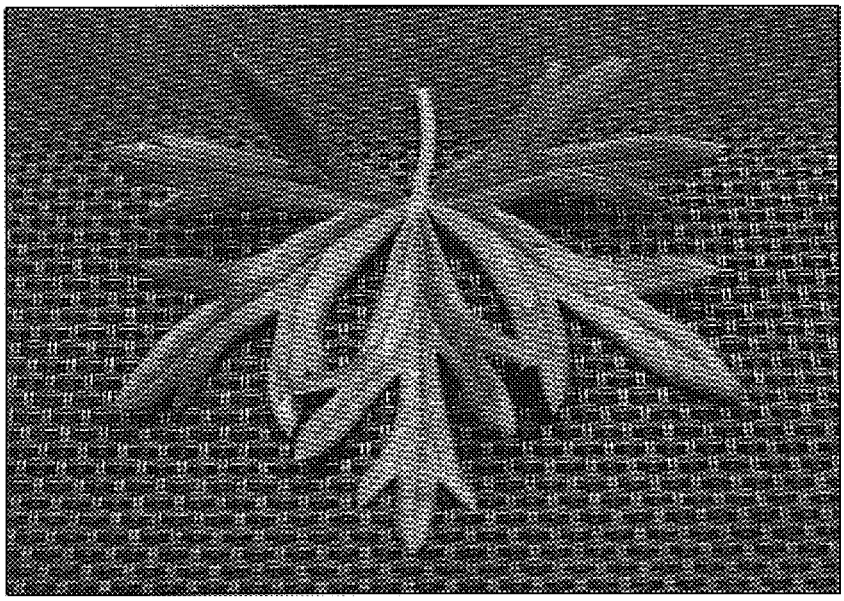
FIG. 3 shows a close-up of a mature leaf.

The following detailed descriptions set forth the distinctive characteristics of 'Blue Lagoon'. The data which define these characteristics were collected from asexual reproductions carried out in the Netherlands. The plant history was taken on one year old plants in 17 inch pots in August under normal outdoor light levels with a daily temperature range of 14° C. to 32° C. and a nightly temperature range of 8° C. to 16° C. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Ranunculaceae.
- *Botanical.*—*Aconitum* (interspecific hybrid).
- *Common name.*—Monkshood or wolfsbane.

Parentage:
- *Female parent.*—*Aconitum cammarum* 'Bicolor' (unpatented).
- *Male parent.*—*Aconitum henryi* 'Spark's Variety' (unpatented).

Plant:
- *Type.*—Herbaceous perennial.
- *Shape.*—Narrow triangular.
- *Growth and branching habit.*—Narrow and upright with no branching; flowering stems grow directly from the base; no pinching required.
- *Height.*—29.4 cm.
- *Width.*—20.1 cm.
- *Growth rate* (*Spring*).—About 8.0 cm per month.
- *Propagation.*—Tissue culture.

*Time to produce a finished flowering plant.*—About 6 months.
*Plant vigor.*—Slow to moderate.
*Root description.*—Tubers are narrow ovate, 4.3 cm in length, 0.5 cm in width, dull, slightly rough to the touch and RHS 164C (greyed-orange) in color.
*Hardiness.*—Hardy to at least USDA zone 4.

Stems:
*Quantity.*—One.
*Length* (*excluding inflorescence*).—17.6 cm.
*Diameter.*—0.3 cm.
*Shape.*—Rounded.
*Appearance.*—Smooth and slightly glossy.
*Pubescence.*—Absent.
*Internode length.*—0.8 cm.
*Color.*—RHS 137C to RHS 137D (green).
*Strength.*—Strong.

Leaves:
*Arrangement.*—Alternate.
*Type.*—Single.
*Quantity.*—23 per stem.
*Size.*—Length: 7.3 cm. Width: 8.2 cm.
*Shape.*—Pedately lobed and lobes are laciniate but overall shape of leaf is cordate.
*Apex.*—Acute.
*Base.*—Hastate.
*Margin.*—Entire.
*Color* (*immature leaves*).—Upper surface: RHS 143A (green). Lower surface: RHS 138B (green).
*Color* (*mature leaves*).—Upper surface: RHS 137A (green) but slightly darker. Lower surface: RHS 138B (green).
*Appearance.*—Slightly glossy, veins furrowed.
*Pubescence.*—Absent.
*Durability of leaves to stress.*—High.
*Venation pattern.*—Palmate.
*Venation color.*—Upper surface: RHS 137A (green). Lower surface: RHS 144A (yellow-green).
*Petioles.*—Length: 3.4 cm. Diameter: 0.2 cm. Color: RHS 143A (green) to RHS 144A (yellow-green).

Flower buds:
*Quantity per stem.*—12.
*Bud color.*—RHS 145A (yellow-green) to RHS 145B (yellow-green).
*Length.*—0.8 cm.
*Diameter.*—0.7 cm.
*Height.*—1.3 cm.
*Shape.*—Ovate, upper half is flattened.

Inflorescence:
*Blooming habit.*—Once a year from summer into autumn; flowers are self cleaning; approximately 75% of the flowers in a raceme are open at a given time.
*Arrangement.*—Terminal raceme.
*Height.*—11.8 cm.
*Width.*—6.7 cm.
*Quantity of flower per inflorescence.*—12.
*Lastingness of individual blooms on the plant.*—About 10 days.
*Fragrance.*—Absent.
*Peduncle.*—Color: RHS 137C (green) to RHS 137D (green). Angle: Straight (at 0°) and upright; secondary peduncles are at an average of 30°. Size: Length: 5.9 cm. Diameter: 0.2 cm. Strength: Strong. Quantity per plant: About 4, situated in the upper leaf axils.

Flowers:
*Shape.*—Galeate.
*Aspect.*—Outward.
*Diameter.*—2.0 cm.
*Height.*—2.9 cm.
*Pedicel.*—General: On each pedicel are two small, ovate-shaped oppositely placed bracts that are 0.2 cm in length, 0.1 cm wide and RHS 137B (green) to RHS 137C (green). Length: 3.5 cm. Diameter: 0.15 cm. Angle: About 10 degrees. Strength: Strong. Color: RHS 137C (yellow-green) to RHS 137D (yellow-green).

Tepals:
*General.*—Composed of 5 unfused tepals; one upper hooded tepal, two middle tepals and two lower tepals; two spurs are visible inside the hooded tepal and are 2.2 cm in length, 0.2 cm in width, RHS N92A (violet-blue) and each spur holds a small RHS 197A (greyed-green) nectary.
*Arrangement.*—Rotate.
*Texture.*—Margins are sparsely covered with short, thin hairs that are 0.02 cm in length and RHS N155A (white).
*Appearance.*—Dull.
*Shape.*—Upper tepal: Hooded. Middle tepals: Obovate. Lower tepals: Ovate.
*Apex.*—Broadly acute.
*Base.*—Cuneate.
*Margin.*—Entire.
*Length.*—Upper tepal: 1.9 cm. Middle tepals: 1.9 cm. Lower tepals: 1.4 cm.
*Width.*—Upper tepal: 1.4 cm. Middle tepals: 1.8 cm. Lower tepals: 0.7 cm.
*Color.*—Upper surface, when opening: Upper tepal: RHS 92A (violet-blue) with RHS 144B (yellow-green) to RHS 144C (yellow-green) tips. Middle tepals: RHS N89C (violet-blue) to RHS N89D (violet-blue) with a lighter base of RHS 90D. Lower tepals: RHS 90B (violet-blue) to RHS 90C (violet-blue) with RHS 143B (green) tips. Lower surface, when opening: Upper tepal: RHS 93B (violet-blue) with RHS 144A (yellow-green) tips. Middle tepals: RHS 93B (violet-blue) with a lighter base of RHS 93C. Lower tepals: RHS 92A (violet-blue) with RHS 143B (green) tips. Upper surface, fully open: Upper tepal: RHS 92A (violet-blue) with RHS 144B (yellow-green) to RHS 144C (yellow-green) tips. Middle tepals: RHS N89C (violet-blue) to RHS N89D (violet-blue) with a lighter base of RHS 90D. Lower tepals: RHS 90B (violet-blue) to RHS 90C (violet-blue) with RHS 143B (green) tips. Lower surface, fully open: Upper tepal: RHS 93B (violet-blue) with RHS 144A (yellow-green) tips. Middle tepals: RHS 93B (violet-blue) with a lighter base of RHS 93C. Lower tepals: RHS 92A (violet-blue) with RHS 143B (green) tips.
*Color fading.*—None.

Reproductive organs:
*Stamens.*—Quantity: 30. Anthers: Shape: Broad oblong to kidney shaped, basifixed. Length: 0.1 cm. Length of filament: 0.9 cm. Color of filament: RHS 93C (violet-blue), lower half is pure white and whiter than RHS 155A. Color: RHS 198A (greyed-green). Pollen color: RHS 155A (white). Pollen amount: Sparse.

*Pistils.*—Quantity: 3. Length: 0.25 cm. Stigma: Color: RHS 93A (violet-blue). Shape: Pointed. Style: Length: 0.2 cm. Color: RHS 144B (yellow-green) to RHS 144C (yellow-green). Ovary: Color: RHS 144B (green) to RHS 144C (green).

Fruit and seed set: No seed set observed.

Disease and insect resistance: No more susceptible to pests and diseases than other *Aconitum* varieties.

COMPARISON WITH PARENTAL AND COMMERCIAL CULTIVARS

'Blue Lagoon' differs from the female parent *Aconitum cammarum* 'Bicolor' (unpatented, no Plant Breeder's Rights) by having a significantly shorter plant height.

'Blue Lagoon' differs from the male parent *Aconitum henryi* 'Spark's Variety' (unpatented, no Plant Breeder's Rights) by having a significantly shorter plant height.

'Blue Lagoon' differs from the commercial cultivar 'Royal Flush' (U.S. Plant Pat. No. 16,102) by having a significantly shorter plant height ('Blue Lagoon' is 29.4 cm in height while 'Royal Flush' is 70 cm in height), a smaller leaf size ('Blue Lagoon' has a leaf length of 7.3 cm and a width of 8.2 cm while 'Royal Flush' has leaf length of 14.6 cm and a width of 15.2 cm) and a shorter inflorescence ('Blue Lagoon' has an inflorescence height of 11.8 cm while 'Royal Flush' has an inflorescence height of 20 cm). 'Blue Lagoon' has tepals, while 'Royal Flush' does not have tepals. Additionally, 'Blue Lagoon' has violet-blue flowers, while 'Royal Flush' has dark blue flowers.

'Blue Lagoon' differs from the commercial cultivar 'Pink Sensation' (U.S. Plant Pat. No. 12,661) by having a significantly shorter plant height ('Blue Lagoon' is 29.4 cm in height while 'Pink Sensation' is 70 cm in height) and a smaller leaf size ('Blue Lagoon' has a leaf length of 7.3 cm and a width of 8.2 cm while 'Pink Sensation' has a leaf length of 9.0 cm and a width of 12.0 cm). 'Blue Lagoon' has tepals, while 'Pink Sensation' does not have tepals. 'Blue Lagoon' has violet-blue flowers, while 'Pink Sensation' has pink flowers.

I claim:

1. A new and distinct cultivar of *Aconitum* plant as shown and described herein.

* * * * *